US00PP28563P2

(12) United States Plant Patent
Danziger

(10) Patent No.: US PP28,563 P2
(45) Date of Patent: Oct. 24, 2017

(54) **NEW GUINEA *IMPATIENS* PLANT NAMED 'DHARBABPNK'**

(50) Latin Name: *Impatiens hawkeri*
Varietal Denomination: DHARBABPNK

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 5 days.

(21) Appl. No.: 14/999,082

(22) Filed: Mar. 28, 2016

(51) Int. Cl.
*A01H 5/02* (2006.01)

(52) U.S. Cl.
USPC ..... Plt./318.4

(58) Field of Classification Search
USPC ..... Plt./318.1, 318.4, 318.5
See application file for complete search history.

*Primary Examiner* — Susan McCormick Ewoldt
(74) *Attorney, Agent, or Firm* — Cassandra Bright

(57) ABSTRACT

A new and distinct *Impatiens* cultivar named 'DHARBABPNK' is disclosed, characterized by large light pink flowers, well branched plant form and good sun resistance. The new variety is an *Impatiens*, normally produced as an outdoor garden or container plant.

2 Drawing Sheets

Latin name of the genus and species: *Impatiens hawkeri.*
Variety denomination: 'DHARBABPNK'.

BACKGROUND OF THE INVENTION

The new cultivar is the product of chance discovery. The new variety originated as a naturally occurring branch mutation of the unpatented proprietary variety *Impatiens* 'BM-10-1138'.

The new variety was discovered in November of 2012 by the inventor Gavriel Danziger a citizen of Israel in a research greenhouse in Moshav Mishmar Hashiva, Israel.

Asexual reproduction of the new cultivar was performed by leaf cuttings. The cuttings are from an apical bud that has no more than two expanded leaves and three to four immature leaves present. This was first performed at a research greenhouse in Moshav Mishmar Hashiva, Israel in November of 2012 and has shown that the unique features of this cultivar are stable and reproduced true to type in multiple successive generations.

SUMMARY OF THE INVENTION

The cultivar 'DHARBABPNK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHARBABPNK' These characteristics in combination distinguish 'DHARBABPNK' as a new and distinct *Impatiens* cultivar:

1. Large flowers.
2. Unique pink flower color.
3. Well branched plants.
4. Distinctive resistance to sunny conditions.

Plants of the new cultivar 'DHARBABPNK' are similar to plants of the parent, *Impatiens* in most horticultural characteristics, however, plants of the new cultivar 'DHARBABPNK' differ in the following;

1. The new variety has pink flowers while the parent has purple colored flowers.
2. The new variety has larger flowers than the parent.

COMMERCIAL COMPARISON

Plants of the new cultivar 'DHARBABPINK' are comparable to the commercial variety *Impatiens* 'DHARSDPINK', patent pending, U.S. Plant Pat. No. 27,634. The two *Impatiens* varieties are similar in most horticultural characteristics; however, the new variety 'DHARBABPNK' differs in the following:

1. Flower color of the new variety is darker.
2. Leaf color of the new variety is darker.
3. Growth habit of the new variety is more compact.

Plants of the new cultivar 'DHARBABPNK' can also be compared to the patented commercial variety *Impatiens* 'SAKIMP013' U.S. Plant Pat. No. 19,597. The two *Impatiens* varieties are similar in most horticultural characteristics; however, the new variety 'DHARBABPNK' differs in the following:

1. Flower color of the new variety is lighter than the comparator.
2. Leaf color of the new variety is lighter than leaf color of the comparison variety.
3. Growth habit of the new variety is more compact than growth habit of the comparator.

BRIEF DESCRIPTION OF THE PHOTOGRAPHS

Figure 1:
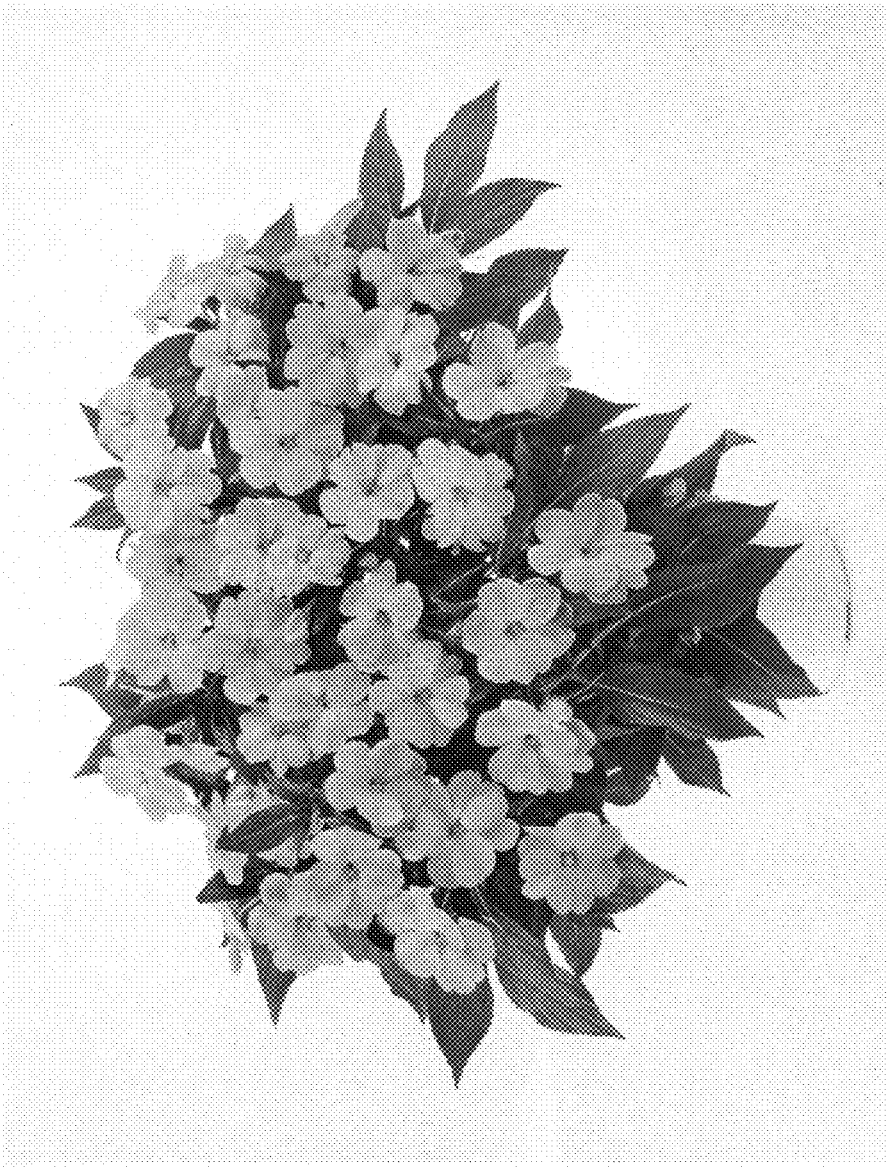

The accompanying photograph in FIG. 1 illustrates in full color a typical plant of 'DHARBABPNK' grown in a greenhouse, in a 16 cm pot. Age of the plant photographed is approximately 14 weeks from a rooted cutting.

Figure 2:
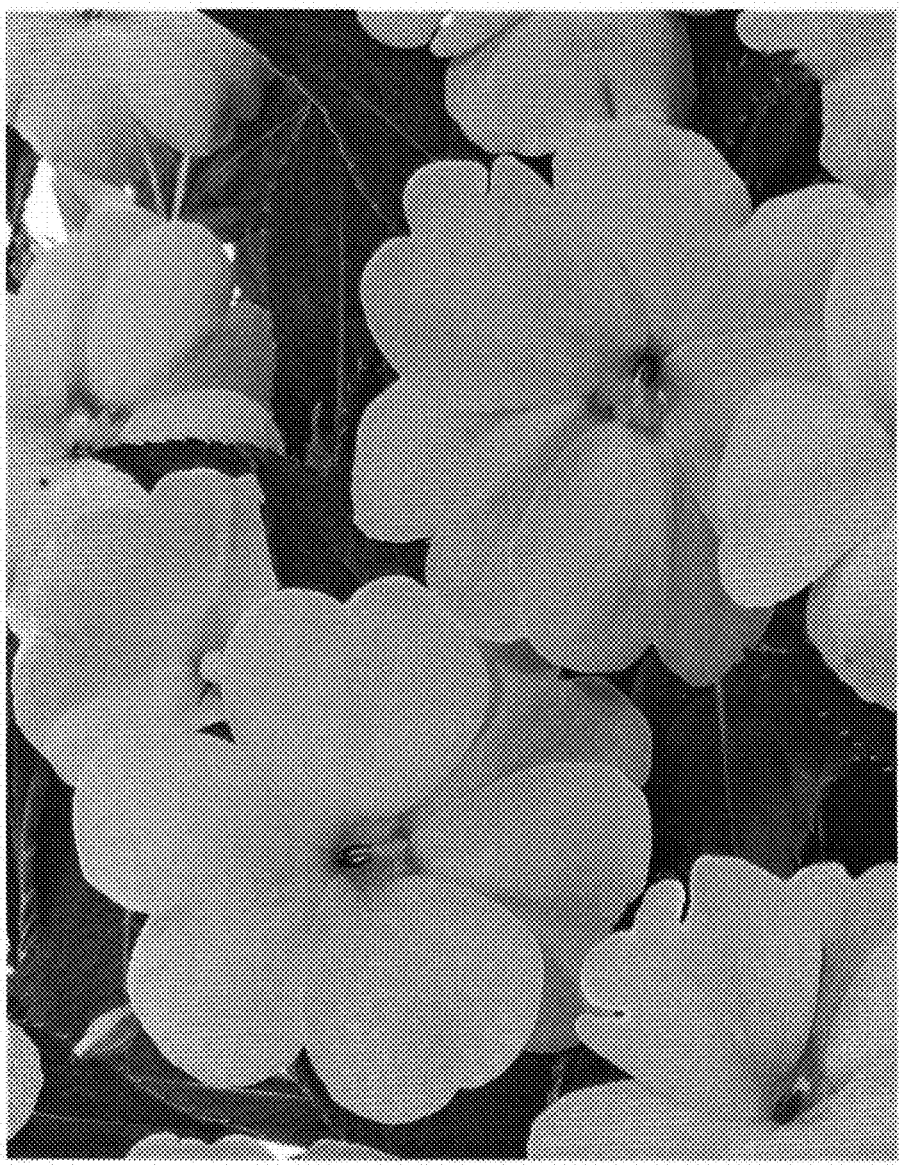

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DHARBABPNK' plants grown in the Autumn, in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: *Impatiens* 'DHARBABPNK'.

PROPAGATION

Type of propagation typically used: Vegetative cuttings.

Time to initiate roots: 10-14 days in Summer, 14-20 days in Winter.

Root description: Fibrous adventitious roots.

PLANT

Age of plant described: Approximately 14 weeks.

Container size of the plant described: 16 cm.

Growth habit: Mounded.

Height: 27-30 cm.

Plant spread: 40 cm.

Growth rate: Vigorous.

Branching characteristics: Very well branched.

Length of primary lateral branches: 20 to 25 cm.

Quantity of primary lateral branches: 5-10.

Characteristics of primary lateral branches:

*Form*.—Oval shape.

*Diameter*.—1 cm.

*Color*.—Near RHS Yellow-Green 146B.

*Texture*.—Smooth.

*Strength*.—Strong, very sturdy.

Internode length: 5 cm.

FOLIAGE

Leaf:

*Arrangement*.—Alternate.

*Quantity*.—Approximately 15-20 per branch.

*Average length*.—8 cm.

*Average width*.—3.5 cm.

*Shape of blade*.—Oblanceolate.

*Apex*.—Apiculate.

*Base*.—Acuminate.

*Margin*.—Ciliate.

*Texture of top surface*.—Smooth.

*Texture of bottom surface*.—Smooth.

*Pubescence*.—None.

*Aspect*.—Mainly flat, attached at approximately 45 degrees.

*Color*.—Young foliage upper side: Near RHS Green 137B. Young foliage under side: Near RHS Green 137D. Mature foliage upper side: Near RHS Green 137A. Mature foliage under side: Near RHS Yellow-Green 147B.

*Venation*.—Type: Pinnate. Venation color upper side: Near RHS Yellow-Green 147B. Venation color under side: Near RHS Green 138D.

*Petiole*.—Length: 1 cm. Diameter: 0.5 cm. Color: Near RHS Yellow-Green 145C. Texture: Smooth.

FLOWER

Natural flowering season: Flowers at any day length. All year round in a greenhouse environment. Flowering is continuous from spring until fall in an outdoor garden.

Days to flowering from rooted cutting: 10 weeks.

Inflorescence and flower type and habit: Single flowers raised above the foliage. The corolla consists of five petals.

Rate of flower opening: 5 to 15 days from bud to fully opened flower.

Flower longevity on plant: 5-8 days.

Persistent or self-cleaning: Self-cleaning.

Bud:

*Shape*.—Ovate.

*Length*.—2 cm.

*Diameter*.—1.5 cm.

*Color*.—Near RHS Red-Purple 62C.

Flower size:

*Diameter*.—7 cm.

*Depth*.—Approximately 2.0 cm, excluding spur.

Petals:

*Quantity*.—5.

*Arrangement*.—Overlapping.

*Length*.—3.5 to 4.0 cm.

*Width*.—3.5 cm.

*Shape*.—Obcordate.

*Apex*.—Cordate.

*Base*.—Acute.

*Margin*.—Entire.

*Texture, upper and lower surfaces*.—Smooth.

*Color*.—When opening, upper surface: Primary color near Red 55A. Secondary Color near Red-Purple N66A. When opening, lower surface: Near RHS Red-Purple 63C. Fully opened, upper surface: Primary color near RHS Red-Purple 62A. Towards base near colored near N66B, faint flush at base near Purple 76A. Fully opened, lower surface: Near RHS Red-Purple 62B.

Spurs:

*Quantity per flower*.—1.

*Length*.—5.5 cm

*Diameter*.—0.2 cm

*Aspect*.—Spur curvature 40°-45° from peduncle.

*Color*.—Towards base: Near RHS Red 54C. Apex: Near RHS Yellow-green 144B and N144D. Both colors present individually.

Sepals:

*Quantity*.—2.

*Length*.—1.5 cm

*Width*.—0.8 cm

*Shape (overall)*.—Oblong. Apex: Caudate. Base: Rounded.

*Margin*.—Entire.

*Texture, upper and lower surfaces*.—Smooth.

*Color*.—Near RHS Yellow-green 145C.

Peduncles:

*Length*.—5.0 cm.

*Diameter*.—0.3 cm.

*Angle*.—About 45° to the lateral branch.

*Strength*.—Stable, flexible.

*Texture*.—Smooth.

*Color*.—Near RHS Yellow-green 145C.

Fragrance: None.

REPRODUCTIVE ORGANS

Stamens: There are five stamens with anthers that are more or less fused and form a cap over the ovary.

*Number*.—5.

Anthers:

*Shape*.—Oblong.

*Length*.—Approximately 0.8 cm.

*Color*.—Near RHS Red-purple 63D.

*Pollen*.—Color: Near RHS White 155D. Quantity: Sparse.

Pistil:

*Number*.—1.

*Length*.—0.5 cm.

*Style*.—Length: 0.5 cm. Color: Near RHS Yellow-green 145C.

*Stigma*.—Shape: Round. Color: Near RHS White 155D. Ovary Color: Near RHS Yellow-green 149D.

OTHER CHARACTERISTICS

Seeds and fruits: 5-10 seeds per fruit.

Disease/pest resistance: Neither resistance nor susceptibility to normal diseases and pests of *Impatiens* have been observed.

Temperature tolerance: Tolerant at 30° C. and tolerant at 5° C. degrees Celsius (grows best at 10° C.-28° C.).

What is claimed is:

1. A new and distinct cultivar of *Impatiens* plant named 'DHARBABPNK' as herein illustrated and described.

* * * * *